(12) United States Patent
Svetliza et al.

(10) Patent No.: US 6,309,070 B1
(45) Date of Patent: Oct. 30, 2001

(54) INTEGRATED OPHTHALMIC ILLUMINATION METHOD AND SYSTEM

(75) Inventors: Eduardo Svetliza, Caesarea; Oded Wigderson, Haifa; Shimon Peled, Kiryat Haim, all of (IL)

(73) Assignee: Medibell Medical Vision Technologies, Ltd., Haifa (IL)

( * ) Notice: Subject to any disclaimer, the term of this patent is extended or adjusted under 35 U.S.C. 154(b) by 0 days.

(21) Appl. No.: 09/656,428

(22) Filed: Sep. 6, 2000

(51) Int. Cl.[7] .................................................. A61B 3/10
(52) U.S. Cl. ................................................................ 351/221
(58) Field of Search .................................... 351/205, 206, 351/221, 210, 211, 216, 220, 209; 606/4

(56) References Cited

U.S. PATENT DOCUMENTS

| | | | |
|---|---|---|---|
| 4,781,453 | * 11/1988 | Kobayashi | 351/205 |
| 5,997,141 | * 12/1999 | Heacock | 351/221 |
| 6,099,127 | * 8/2000 | Manivannan et al. | 351/221 |

* cited by examiner

Primary Examiner—George Manuel
(74) Attorney, Agent, or Firm—Edward Langer, Pat. Atty.

(57) ABSTRACT

An integrated ophthalmic illumination method and system having two integrated light sources, a lamp and an infra-red (IR) diode laser. The lamp light source may be used to produce either monochromatic or color images, as necessary, at high resolution. In a preferred embodiment, color images are provided using an RGBT (red-green-blue-transparent) filter wheel. The filter wheel is divided into four sections or arc sections around the periphery of the wheel. Three of the four partitioned sections are larger and equal sections that comprise the three optical R, G and B filter sections. The fourth section is a transparent, or empty, narrow section that is used for transferring the full original content of the white beam when a monochromatic or chromatic image is desired. The RGBT wheel rotates at a speed of one third of the frame rate of a CCD camera, producing a sequence of definite R, G and B spectral light bursts. These R, G and B illuminated images are later composed by a computer into a single colored picture. A second filter wheel is provided with several spaced filters mounted around a disc which allow for use in monochromatic illumination and excitation with angiographic agents.

19 Claims, 5 Drawing Sheets

INTEGRATED OPHTHALMIC ILLUMINATION METHOD AND SYSTEM

FIELD OF THE INVENTION

This invention relates to an integrated ophthalmic illumination method and system and more particularly, to an illuminating device providing both white and laser light sources, to be used as needed. The inventive device has in its illumination path a color filter plate that is divided into a plurality of filter sections for producing a high resolution color image using a monochromatic camera, making it capable of monochromatic imaging and excitation of fluorescent dyes.

BACKGROUND OF THE INVENTION

Currently, many color images are produced for various medical purposes using either single chip color video cameras or color cameras with 3 charge-coupled devices (CCDs), each of the CCDs being monochromatic and representing one of the primary colors R (red), G (green), and B (blue). The method of use of a single chip color camera is limited in resolution, since each pixel is dedicated to only one of the colors. The resolution obtained, therefore, would be significant lower.

Three-chip CCD cameras may be used for the production of monochrome as well as color images. However, prices for such a camera are significantly high, thus precluding the production of images with resolutions above 512×512 pixels.

In order to maximize resolution, a different method is used in which an illuminating means sequentially irradiates light of the three primary colors to illuminate the eye. The imaging signals are read in synchronism with the TV camera frame integration cycle for each color and are processed by a computer to display the image in color. This sequential color imaging has the advantage that it produces an image with high resolution, using a relatively inexpensive monochromatic single chip camera.

However, some procedures (e.g. fundus examination with indocyanine green (ICG)) require stronger light than that provided by a conventional light source, such as a non-coherent light. Prior art devices use flash pulse photography to get single frame photographs of the image desired. This often results in low-resolution images when an inadequate intensity of pulse is applied. Also, there are many cases where dynamic imaging is necessary and cannot be obtained with flash pulse photography.

A laser light could provide a continuous light source, however, the light intensity of a laser is undesirable for some uses because of its strength and the heat which it generates which raise safety issues regarding direct application to the eye. Therefore, it is necessary to decollimate the laser light. An infrared fundus video angiography system is provided in U.S. Pat. No. 5,400,791 to Schlier et al. having a decollimated laser light, however no monitoring is provided for ascertaining the safety of the light intensity passing through the system.

Thus, it would be desirable to provide a cost-efficient illumination system for high resolution monochrome or color-imaging in optical diagnostic equipment, integrating both conventional incandescent and laser light sources, both sources being monitored by a computer feedback system for precise and safe operation for a variety of uses.

SUMMARY OF THE INVENTION

It is a principal object of the present invention to overcome the disadvantages associated with conventional illumination systems for optical diagnostic equipment, and provide a high resolution imaging system with alternative illumination sources.

In accordance with a preferred embodiment of the present invention there is provided a method for integrated ophthalmic illumination comprising the steps of:

providing a light source producing a light beam;

separating red, green and blue components of said light beam;

sequentially illuminating the eye with said separated red, green and blue components at a rate of one component per frame;

imaging said sequentially illuminated subject;

processing said sequential color images such that said separated red, green and blue components are combined so as to obtain a high resolution color image.

There is also provided an integrated ophthalmic illumination system comprising:

a first light source, said first light source being a lamp;

first collimating optics, to provide a collimated light beam from said first light source;

a first light intensity monitor for monitoring said collimated light beam;

a second light source, said second light source being a coherent light source;

second collimating optics, to provide a collimated coherent light beam from said second light source;

a second light intensity monitor for monitoring said collimated coherent light beam;

a separation unit for separating red, green and blue components of said collimated light beam, so as to produce sequential color images;

a computer processor; and an electronic image capturing sensor, said computer processor taking said sequential color images obtained using one of said first and said second light sources and forming therefrom at least one of a high resolution color and monochromatic image.

In the preferred embodiment of the invention, there is provided an illumination system having two integrated light sources, a lamp (including but not limited to a tungsten, metal halide or halogen lamp or any type of filament or gas lamp) and a coherent light beam such as an infrared (IR) diode laser. In a preferred embodiment, color images are provided using an RGBT (red-green-blue-transparent) filter wheel. The filter wheel is divided into four sections or arc sections around the periphery of the wheel. Three of the four partitioned sections are larger and equal sections that comprise the three optical R, G and B filter sections. The fourth section is a transparent, or empty, narrow section that is used for transferring the full original content of the white beam when a monochromatic or chromatic image is desired. The RGBT wheel rotates at a speed of one third of the frame rate of a CCD camera, producing a sequence of definite R, G and B spectral light bursts. These light bursts illuminate the interior of the eye, enabling a whole image of the eye fundus to be reflected out and detected by the image capturing sensor. These R, G and B illuminated images are later composed by a computer into a single colored picture.

In an alternative embodiment, similar color splitting is accomplished by means of an X-cube splitter used to divide the white light into its R, G and B components. In yet another preferred embodiment, a series of three 45° tilted beam splitters or dichroic spectral beam splitters are used to divide the light into three channels, and then the desired wavelengths are filtered from each channel.

A second filter wheel is provided with several spaced filters mounted around a disc which allow for use in monochromatic illumination and excitation with angiographic agents. The filter wheel locks in certain positions where one of the interchangeable filters overlaps the entire beam cross section, thus isolating a certain spectral window from the full "white" content of the beam. This filter wheel is provided with a transparent section to allow full spectral content of said collimated light beam to pass through when a filter is not needed.

Other features and advantages of the invention will become apparent from the following drawings and description.

BRIEF DESCRIPTION OF THE DRAWINGS

For a better understanding of the invention with regard to the embodiments thereof, reference is made to the accompanying drawings, in which like numerals designate corresponding elements or sections throughout, and in which.

DETAILED DESCRIPTION OF A PREFERRED EMBODIMENT

Figure 1:
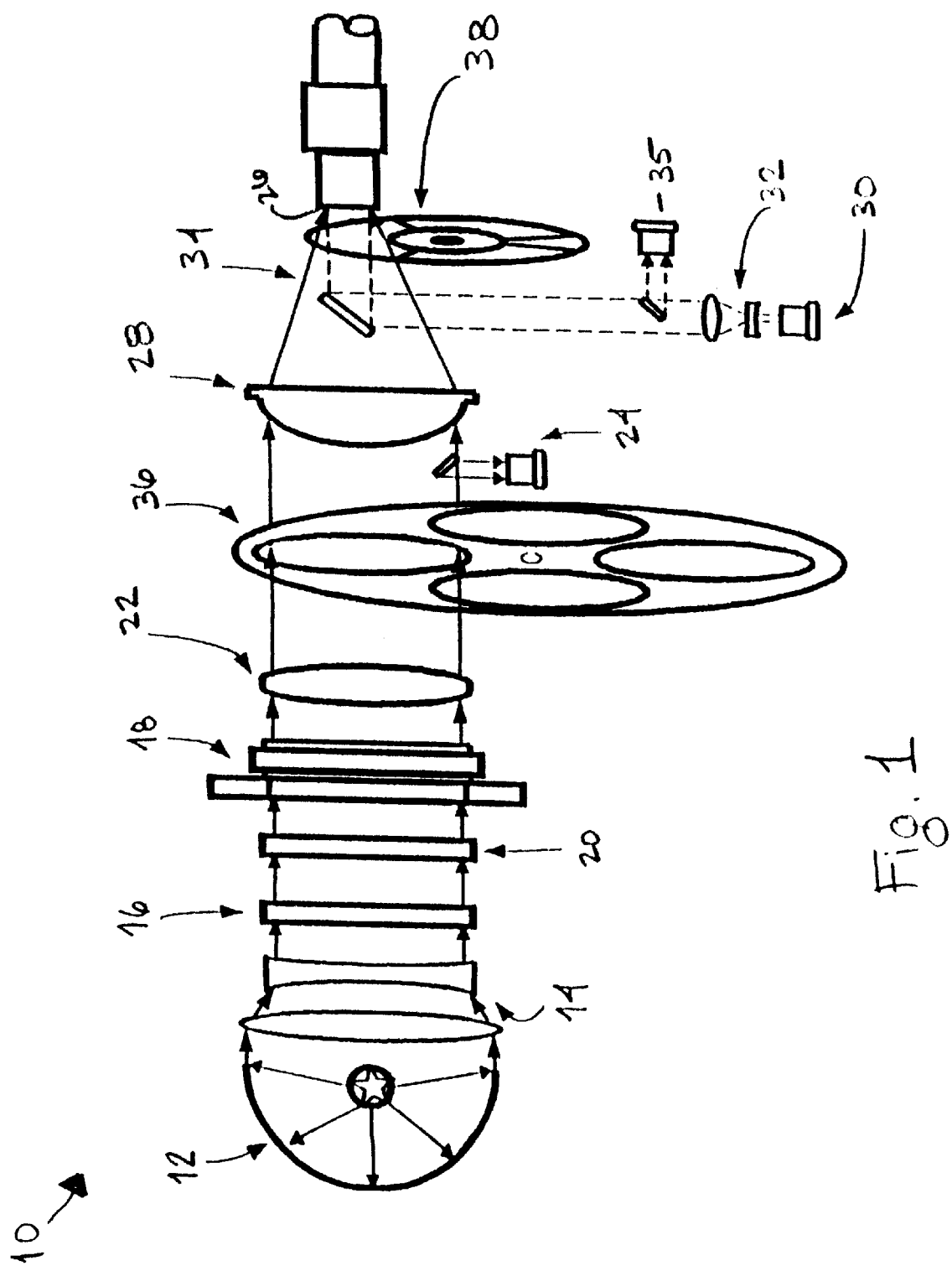
FIG. 1 is a preferred embodiment of the illumination system of the present invention.

Referring now to FIG. 1, there is shown illumination system 10, in which a lamp 12 (by way of example a tungsten, halogen or metal-halide lamp or any type of filament or gas lamp) produces a well defined collimated light beam, with the aid of matching beam-expander optics 14. Hot mirror 16 is placed in the optical path close to the light source to remove ultraviolet (UV) and infrared (IR) components of the light spectral content. Electro-optical fast shutter 18 (by way of example, LCP250 scattering liquid crystal polymer shutter, by Philips, the Netherlands) controls the amount of light in the collimated beam that traverses through the shutter, by changing the shutter light scattering effectiveness (i.e. its direct transmissivity). Neutral density filter 20 may be inserted to enable a more pronounced light power change in the traversing beam. Additional correction optics, e.g. 22, may also be placed downstream of the optical path for beam correction and shaping.

Photodiode 24 monitors the overall light intensity within the optical beam, by means of beam splitter 25 which is introduced into the collimated beam reflecting a small fraction of the main beam light to photodiode 24. This mode of light measurement provides an important safety feature when used with sensitive tissue, such as in the eye.

Towards the end of the light path the collimated beam is focused onto entrance aperture 26 of a fiber optics feeding cable using a short focusing aspheric condensing lens 28. A short focus lens is recommended in order to minimize the beam spot-size dimensions on the entrance aperture plane of the fiber optics bundle guide. Light power of the order of several hundred milliwatts can easily be focused on the output end of the fiber optics feeding bundle.

For some uses conventional light, such as that supplied by lamp 12, is inappropriate, as in the case of certain dyes which must be excited at specific wavelengths, e.g. ICG dye excitation at 800–810 nm. Halogen and metal-halide lamps are relatively weak in their emitted spectral light power content in the longer wavelength regions. To this purpose, an alternative illumination source is provided, such as narrow spectral band IR laser diode 30, which can provide several hundred milliWatts of light power content in a narrow excitation band (e.g. SDL-2350 laser diode, by SDL, USA). When laser diode 30 is in use, lamp 12 is extinguished, and vice versa.

Collimating optics 32 shape and widen the laser light beam to enter fiber optic bundle aperture 26 so that all the fibers will receive light. When ICG is injected into the bloodstream, the dye is 98% absorbed by the plasma protein and has only 4% of the fluorescence efficiency of sodium fluorescein. Due to the poor fluorescence of the dye, a high intensity of IR light is necessary to acquire an acceptable image of high resolution. The intense light projected into the eye must be controlled by second photodiode 35 processed by a computer.

When using IR laser diode 30, electro-optical fast shutter 18 is not required, as control of the light power emitted from such diodes can easily be achieved by monitoring the current driving the diodes or via a TTL modulation feeding circuit that can alter the operational duty cycle of the diode, so as to guard against potential IR light toxicity which can cause retinal tissue injury and impaired vision.

The diode light emission can be delivered directly to fiber-optics bundle aperture 26, by means, for example, of 45° dichroic beam splitter 34. Beam splitter 34 may be placed permanently in the main optical path, since the main path of lamp 12 is not required to convey light spectral components above approximately 750 nm. This allows light of 440–750 nm from the path of lamp 12 to pass through while reflecting the crossed laser beam at the spectral band 780–820 nm toward fiber-optics bundle aperture 26.

When using IR laser diode 30 as the illumination source, the fact that a fiber optics feeding bundle is used to convey the optical light power has an additional benefit. A laser beam traveling through a long fiber optics bundle will lose most of its coherence properties, thus eliminating chances for accidental focused hot spots within the eye tissues. A second photodiode 35 monitors the light from IR laser diode 30, so as to provide a safety feedback. As may be understood by one skilled in the art, by proper positioning of photodiode 35 along the common optical path, second photodiode 35 may replace the task of photodiode 24, as well as its own task, so as to provide a more cost-efficient model.

When lamp 12 is in use, the filters of rotary wheel 36 may be positioned in the optical path for monochromatic illumination. Rotary filter wheel 36 has several spaced filters mounted around a disc. Wheel 36 locks in certain positions where one of the interchangeable filters overlaps the entire beam cross section, thus isolating a certain spectral window from the fill "white" content of the beam. This enables a specified spectral band or colored illumination to illuminate the subject. The monochromatic filters of the rotary wheel may be used also as excitation filters for fluorescein angiography purposes. By way of example, the filter wheel is provided with narrow bandpath optical filters and a transparent (T) or empty window. When filter wheel 36 is locked in position so that the transparent or empty window overlaps the beam cross section, the full power and spectral content of the light beam is allowed for transfer to the next station.

Figure 2:
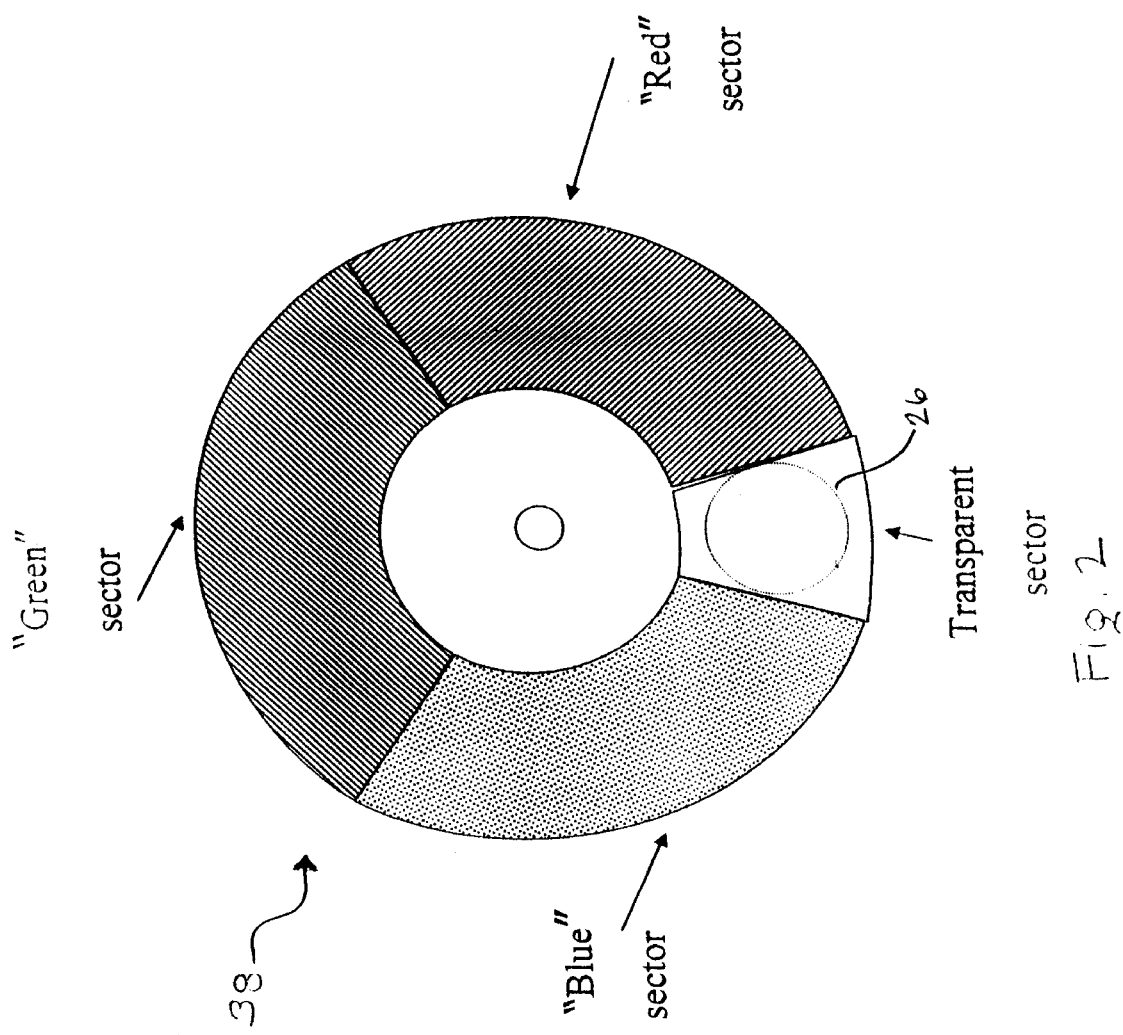
FIG. 2 is the RGBT filter wheel.

In order to enable color imaging without any loss of the high resolution available from a black and white CCD camera, a second RGBT filter wheel 38 is used in the optical path. As shown in FIG. 2, this wheel is divided, by way of example, into 4 partitioned section, the R, G and B sections being larger and equal and a fourth section, the T section which is used for transferring the full original content of the white beam. The dimensions of the T section, at a minimum, overlap the cross-section of fiber optic cable aperture 26.

In order to establish the highest achievable duty cycle for each of the three main R, G and B colored sections, RGBT wheel 38 is preferably positioned close to a plane where the beam is narrowed to a minimum (i.e. near the focal plane of fiber optics outlet port aperture 26). With wheel 38 thus positioned, the projection of the beam cross-section is small, meaning that the T section of the wheel can be at its smallest possible size while still covering aperture 26. This allows the largest duty cycle for the three remaining optically filtered sections, RGB. When RGBT wheel 38 rotates at a speed of one third of the frame rate of the CCD camera, a sequence of definite R, G and B (with a short white) spectral light bursts are transferred to aperture 26 per each revolution of RGBT wheel 38. Each of these R, G or B sequenced light bursts is fully synchronized with one of the consecutive frames of the CCD camera located in the detection channel. This produces R, G and B illuminated images in sequence, each frame of the camera having one color. These images are later composed by the computer into a single colored picture. Thus, every three consecutive monochromatic "colored" images comprise one colored picture. The computer updates these colored pictures at the rate of the camera frame rate, each time a new "colored" frame is detected.

Referring again to FIG. 1, when color pictures are no longer required, RGBT wheel 38 is locked in a position where the T section overlaps the beam cross-section, allowing the full impinging light content from lamp 12 to be passed to aperture 26. When locked in this "white" position, the light can be used for angiography or for specific monochromatic illumination purposes by introducing the appropriate filters into the optical path using filter wheel 36.

Figure 3:
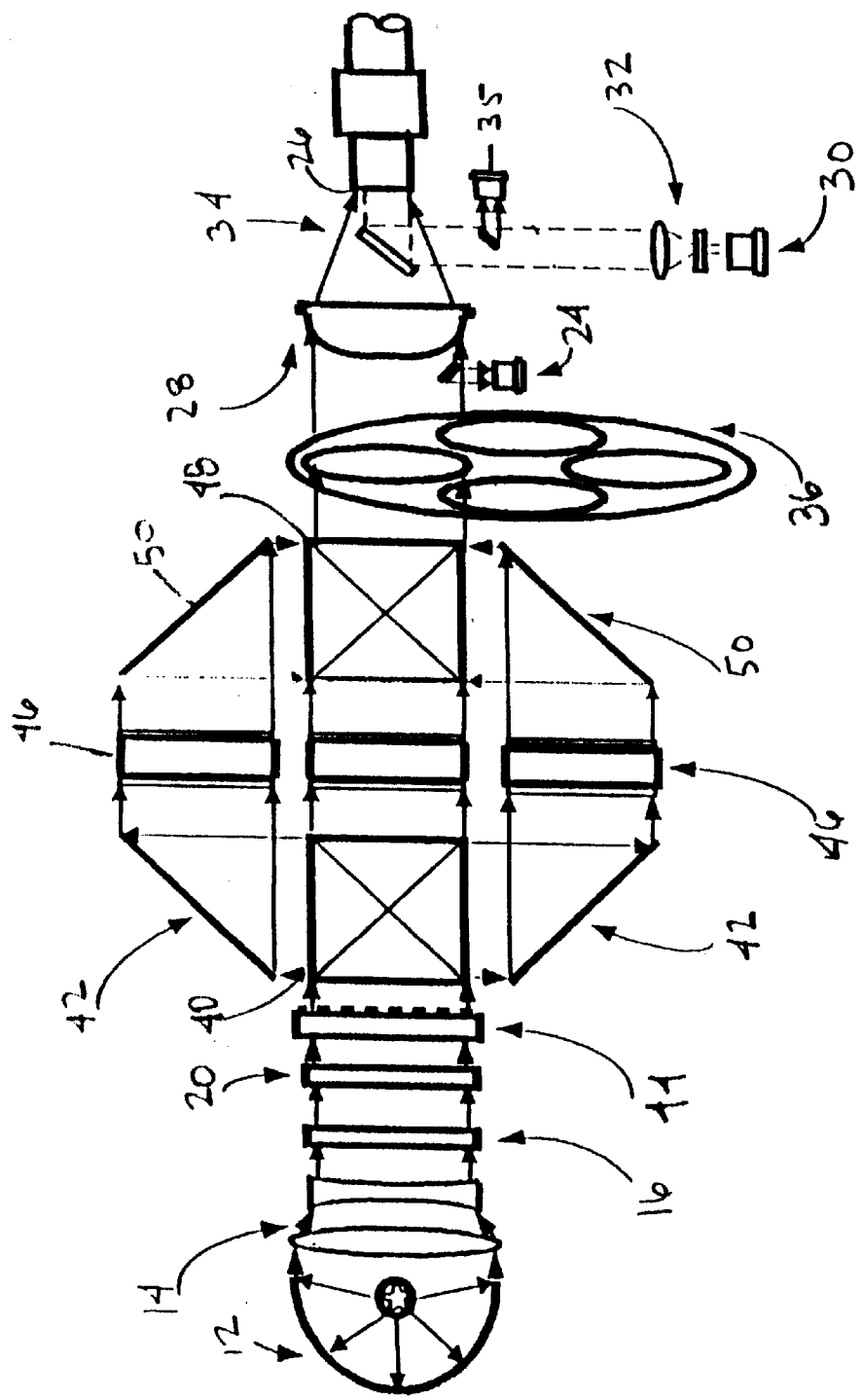
FIG. 3 is an alternative embodiment of the illumination system of the present invention.

As shown in FIG. 3, in an alternative embodiment of illumination system 10, a similar light path is constructed in which a halogen or metal-halide lamp 12 produces a well-defined collimated light beam, with the aid of matching beam-expander optics 14. Hot mirror 16 is placed in the optical path close to the light source to remove ultraviolet (UV) and infrared (IR) components of the light spectral content. In this embodiment, the main beam is split into three "colored" channels (R, G, B) using R-G-B dichroic "X-cube" splitter 40 (by way of example, a 40×40×40 mm SSS Dichroic Prism, Nitto Optical Company, Japan) with two 45° tilted mirrors 42 that deviate the side emerging channel beams to produce three parallel beams. To overcome a possible loss of some polarized light beam components due to polarization sensitivity of X-cube splitter 40, polarization converter prism 44 is inserted in the light path preceding X-cube splitter 40, so as to transform the impinging randomly polarized light beam into a linearly polarized one.

Three electro-optical fast shutters 46 (by way of example, LCP250 scattering liquid crystal polymer shutter, by Philips, the Netherlands) are placed in each of the three split channels to switch on the channels sequentially, each for a duration of one camera frame. Beside the act of switching, shutters 46 are also used for controlling the beam power in each of the channels in order to correctly balance the light power relationship between the three channels.

The three separated channels may be recombined into a single beam by X-cube combiner 48 (by way of example, a 40×40×40 mm SSS Dichroic Prism, Nitto Optical Company, Japan), with the aid of two 45° tilted mirrors 50. When the three (RGB) shutters are operated sequentially, one per each camera frame duration, Red, green and blue light bursts sequentially emerge from X-cube combiner 48. Focusing lens 28 is used to focus the emerged collimated beam onto aperture 26. When colored pictures are not required, all of fast shutters 46 are kept locked in their transparent mode. The combined R, G and B beams constitute a white light beam together that is passed to aperture 26. As in FIG. 1, the white beam illumination can be used for angiography or for specific monochromatic illumination by introducing the appropriate filter into filter wheel 36. The illumination path for laser diode 30 remains the same as in FIG. 1.

Figure 4:
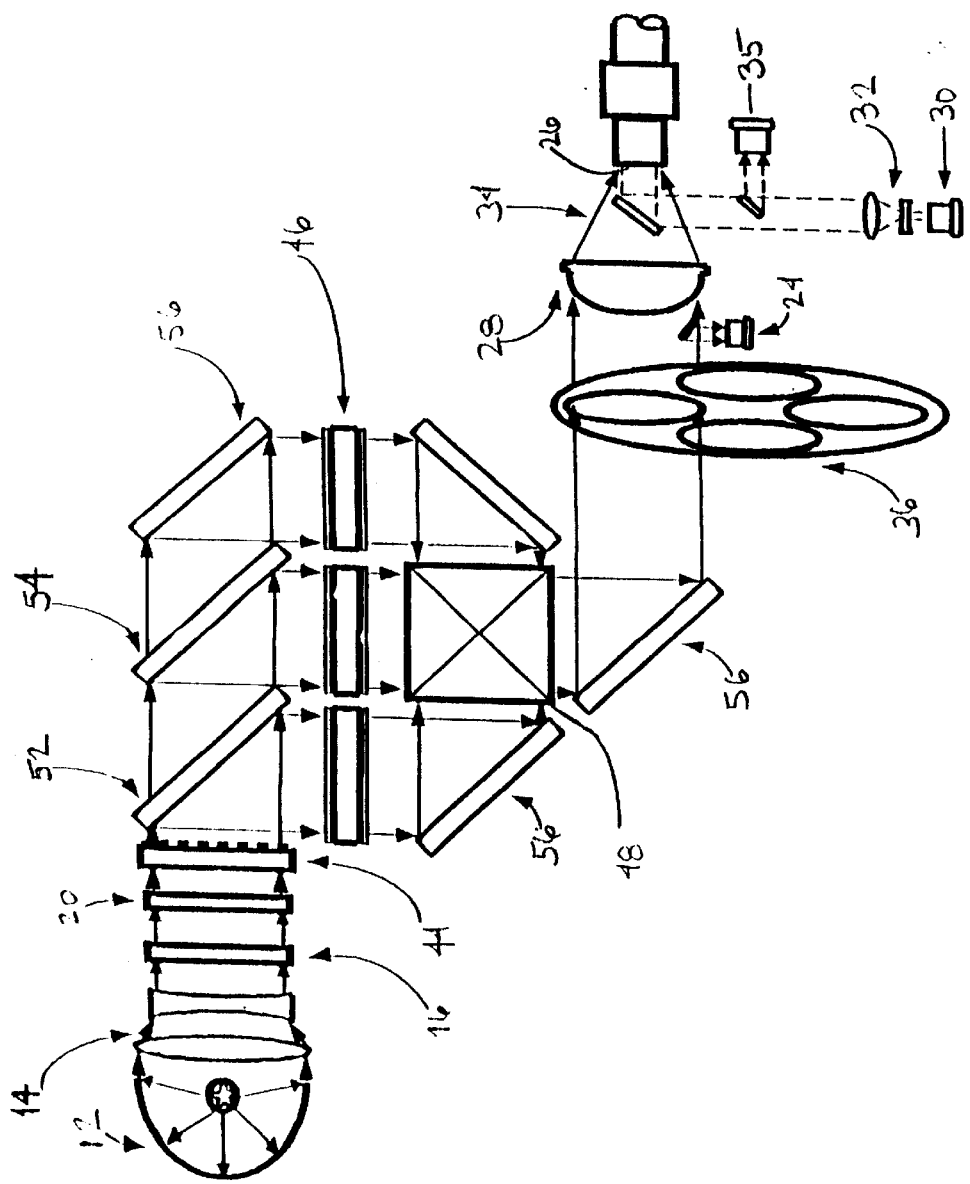
FIG. 4 is a further alternative embodiment of the illumination system of the present invention.

Referring now to FIG. 4, another alternative embodiment of illumination system 10 is shown in which the splitting of the main channel into R, G and B sequential synchronized light bursts is accomplished using a series of three 45° tilted beam splitters: 30R/70T beam splitter 52, 5OR/50T beam splitter 54 and 45° tilted mirror 56 (by way of example, M43-360, M43-359 and M43-876 by Edmund Scientific, New York, USA, respectively), and adding an R, G or B optical filter to each of the channels. Alternatively, a series of three 45° tilted dichroic spectral beam splitters in B, R and G may be used (e.g. J43-454, J43-455 and J43-458 corrector, Edmund Scientific, Barrington, N.J., USA, respectively).

The use of three 45° tilted beam splitters is the least efficient method of color splitting, as compared to the embodiments shown in FIG. 1 and FIG. 3, due to the partitioning of the total beam power into three separated channels with about one third of the total power content in each channel. Therefore, the optical filters in each channel are separating out only part of the spectral content of the already reduced light power in the channel. Once the color splitting has been accomplished, mirrors 44 and X-cube combiner 48 function as described in FIG. 3.

Figure 5:
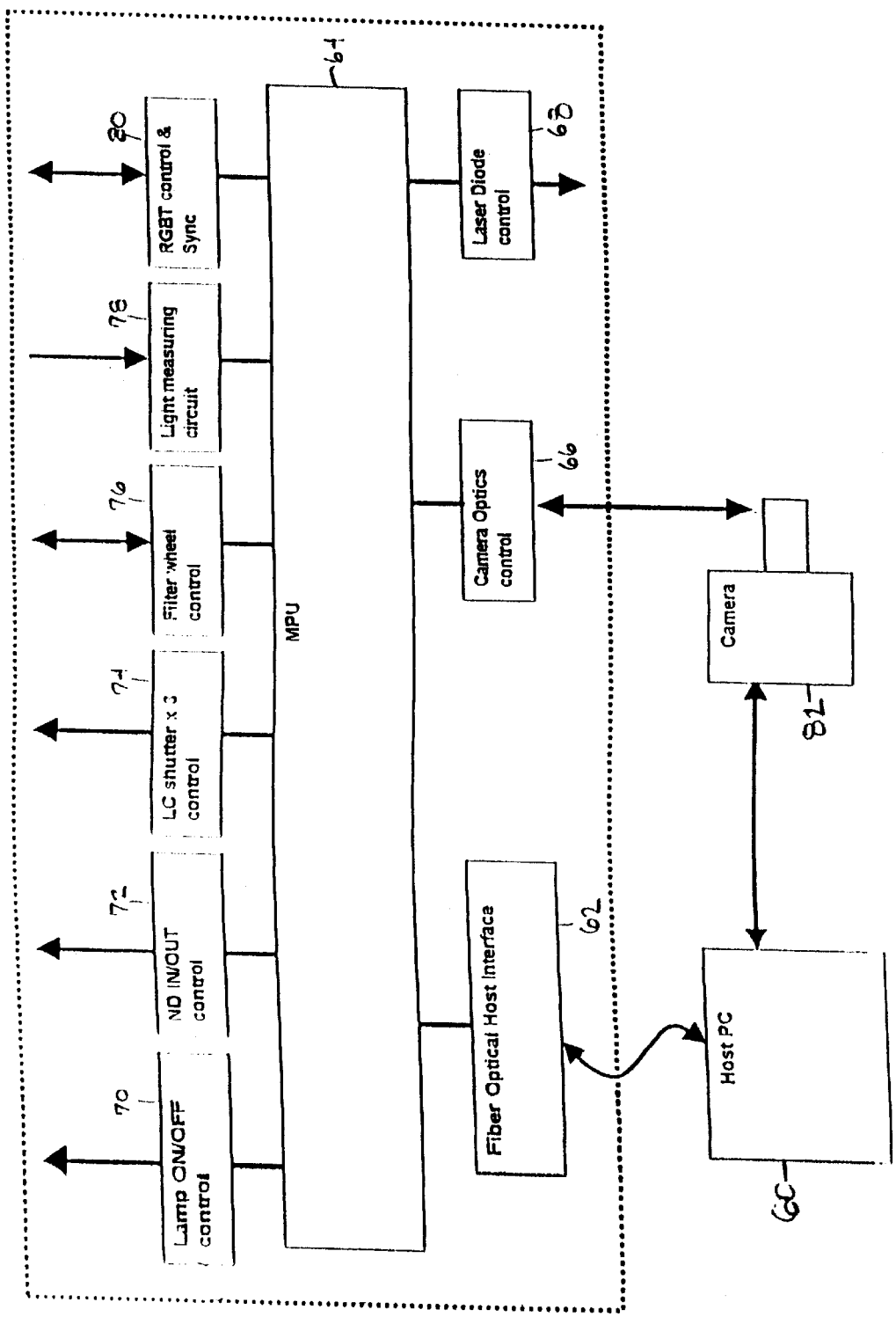
FIG. 5 is a block diagram of the computerized controls of the illumination system of the present invention.

Referring now to FIG. 5, there is shown a block diagram of the computerized controls of illumination system 10, provided as a printed circuit board (PCB) designed to control and monitor the optical parts of illumination system 10 (in any of the embodiments depicted in FIGS. 1, 3 or 4), and interface with host PC 60.

In block 62, the copper to fiber interface between the PC 60 and the illumination system is provided as a fiber optic interface for signal conversion, with communication of up to 100 Mbit/sec, bidirectionally. In block 64, the main processing unit (MPU), which may be, for example an Altera 10 k based type, is in charge of communication with all I/O's and host PC 60. The control algorithms are implemented here.

In block 66 the camera optics control drives four indepenedent motorized mechanisms, responsible for focusing, zooming, depth of focus and filtering. Laser diode 30 is controlled in block 68, while a circuit in block 70 controls lamp 12. This may also be used as an emergency off circuit. Neutral density filter 20 is inserted or removed by block 72 to control light passing therethrough from light source 12. In block 74, there is provided a circuit capable of controlling up to three fast shutters such as 18 or 46, for continuous control frame resolution and color weighing.

The filter wheel control is provided in block 76 and drives rotary filter wheel 36. An 8 channel 10 bit serial analog to digital converter (ADC) is provided in block 78 for measuring light passing through the light source and for monitoring safe light levels in the light measuring circuit. Block 80 is a circuit used to revolve color wheel 38 so it is synchronized to the camera frame integration in color mode, and to position the wheel in its transparent sector in monochromatic and angiography test modes.

Clearly, the present invention may interface with the illumination path of a slit lamp, any kind of opththalmoscope, ophthalmic camera, surgical microscope, endoscope, culposcope, laparascope, or other medical device. In this way these devices become versatile, allowing a wide range of test capability with a single optical system which includes color, monochromatic and angiography imaging ability.

Having described the invention with regard to certain specific embodiments thereof, it is to be understood that the description is not meant as a limitation, since further modifications may now suggest themselves to those skilled in the art, and it is intended to cover such modifications as fall within the scope of the appended claims.

We claim:

1. A method for integrated ophthalmic illumination comprising the steps of;

providing a light source producing a light beam;

separating red, green and blue components of said light beam;

sequentially illuminating the eye region with said separated red, green and blue components at a rate of one component per frame;

imaging said sequentially illuminated subject; and processing said sequential color images such that said separated red, green and blue components are combined so as to obtain a high resolution color image.

2. An integrated ophthalmic illumination system comprising:

a first light source, said first light source being a lamp;

first collimating optics, to provide a collimated light beam from said first light source;

a first light intensity monitor for monitoring said collimated light beam; a second light source, said second light source being a coherent light source; second collimating optics, to provide a collimated coherent light beam from said second light source;

a second light intensity monitor for monitoring said collimated coherent light beam;

a separation unit for separating red, green and blue components of said collimated light beam, so as to produce sequential color images;

a computer processor; and an electronic image capturing sensor, said computer processor taking said sequential color images obtained using one of said first and said second light sources and forming therefrom at least one of a high resolution color and monochromatic image.

3. The illumination system of claim 2 wherein said lamp is one of the group of: filament and gas.

4. The illumination system of claim 2 further comprising a shutter for controlling the amount of light from said collimated light beam.

5. The illumination system of claim 4 wherein said first and second light monitors are provided as a beam splitter and a photodiode, the output of said photodiode being processed by said processor, said processor controlling said shutter accordingly.

6. The illumination system of claim 2 further comprising a neutral density filter.

7. The illumination system of claim 2 further comprising a condensing lens to minimize said collimated light beam.

8. The illumination system of claim 7 further comprising a fiber optics bundle, said minimized collimated light beam being an appropriate size to enter an aperture of said fiber optic bundle.

9. The illumination system of claim 2 wherein said second light source is provided as an IR laser diode.

10. The illumination system of claim 2 wherein said electronic imaging sensor is monochrome.

11. The illumination system of claim 2 wherein said electronic imaging sensor is a color camera.

12. The illumination system of claim 2 wherein said separation unit for separating red, green and blue components of said collimated light beam is provided as a filter wheel.

13. The illumination system of claim 12 wherein said filter wheel is comprised of four filter sections, with sections for red, green and blue being substantially equal in size and said red, green and blue sections being larger than a transparent section.

14. The illumination system of claim 12 wherein said filter wheel rotates at a speed of one-third of the frame rate of said imaging means.

15. The illumination system of claim 2 wherein said separation unit for separating red, green and blue components of said collimated light beam is provided as an RGB dichroic X-cube splitter, said X-cube splitter producing two deviated side emerging channel beams, further comprising two tilted mirrors that deviate said side emerging channel beams to provide two light beams parallel to said collimated light beam, and an X-cube combiner.

16. The illumination system of claim 2 wherein said separation unit for separating red, green and blue components of said collimated light beam is provided as a series of tilted beam splitters.

17. The illumination system of claim 2 further comprising a second filter wheel for use in at least one of monochromatic illumination and excitation with angiographic agents.

18. The illumination system of claim 17 wherein said second filter wheel further comprises a transparent section to allow full spectral content of said collimated light beam to pass through said second filter wheel.

19. The illumination system of claim 2 wherein said coherent light beam is provided at a wavelength of approximately 500 nm, appropriate for the excitation of fluorescein dye.

* * * * *